US00PP22225P2

(12) United States Plant Patent
Elliot

(10) Patent No.: US PP22,225 P2
(45) Date of Patent: Nov. 1, 2011

(54) ***BRACHYCOME* PLANT NAMED 'MAGENTA MAGIC'**

(50) Latin Name: *Brachycome angustifolia*
Varietal Denomination: Magenta Magic

(75) Inventor: Rodger Elliot, Cranbourne (AU)

(73) Assignee: Outback Plants Pty. Ltd., Cranbourne, Victoria (AU)

( * ) Notice: Subject to any disclaimer, the term of this patent is extended or adjusted under 35 U.S.C. 154(b) by 7 days.

(21) Appl. No.: 12/799,848

(22) Filed: May 4, 2010

(51) Int. Cl.
*A01H 5/00* (2006.01)

(52) U.S. Cl. ..... Plt./411

(58) Field of Classification Search ..... Plt./411
See application file for complete search history.

*Primary Examiner* — Susan McCormick Ewoldt
(74) *Attorney, Agent, or Firm* — C. A. Whealy

(57) ABSTRACT

A new and distinct cultivar of *Brachycome* plant named 'Magenta Magic', characterized by its compact, low spreading and mounding plant habit; freely branching growth habit; dark green-colored stems and leaves; freely flowering habit; large inflorescences positioned above the foliar plane; bright purple-colored ray florets; and good postproduction longevity.

2 Drawing Sheets

Botanical designation: *Brachycome angustifolia.*
Cultivar denomination: 'MAGENTA MAGIC'.

BACKGROUND OF THE INVENTION

The present invention relates to a new and distinct cultivar of *Brachycome* plant, botanically known as *Brachycome angustifolia* and hereinafter referred to by the name 'Magenta Magic'.

The new *Brachycome* plant is a product of a controlled breeding program conducted by the Inventor in Cranbourne, Victoria, Australia. The objective of the breeding program is to create new compact *Brachycome* plants with large inflorescences and strong foliage.

The new *Brachycome* plant originated from a cross-pollination in Cranbourne, Victoria, Australia, of a proprietary selection of *Brachycome angustifolia* identified as code name OBAP176, not patented, as the female, or seed, parent with a proprietary selection of *Brachycome angustifolia* identified as code name OB04547, not patented, as the male, or pollen, parent. The new *Brachycome* plant was discovered and selected by the Inventor in July, 2006 as a single flowering plant from within the progeny of the stated cross-pollination in a controlled environment in Cranbourne, Victoria, Australia.

Asexual reproduction of the new *Brachycome* plant by stem cuttings in a controlled environment in Cranbourne, Victoria, Australia since September, 2006, has shown that the unique features of this new *Brachycome* plant are stable and reproduced true to type in successive generations.

SUMMARY OF THE INVENTION

Plants of the new *Brachycome* have not been observed under all possible environmental conditions and cultural practices. The phenotype may vary somewhat with variations in environment and cultural practices such as temperature and light intensity without, however, any variance in genotype.

The following traits have been repeatedly observed and are determined to be the unique characteristics of 'Magenta Magic'. These characteristics in combination distinguish 'Magenta Magic' as a new and distinct cultivar of *Brachycome* plant:

1. Compact, low spreading and mounding plant habit.
2. Freely branching growth habit.
3. Dark green-colored stems and leaves.
4. Freely flowering habit.
5. Large inflorescences positioned above the foliage.
6. Bright purple-colored ray florets.
7. Good postproduction longevity.

Plants of the new *Brachycome* differ from plants of the female parent selection in the following characteristics:

1. Plants of the new *Brachycome* are not as vigorous as plants of the female parent selection.
2. Plants of the new *Brachycome* are more mounding than and not as upright as plants of the female parent selection.
3. Plants of the new *Brachycome* and the female parent selection differ in ray floret color as plants of the female parent selection have bright pink-colored ray florets.

Plants of the new *Brachycome* differ from plants of the male parent selection in the following characteristics:

1. Plants of the new *Brachycome* are more vigorous than plants of the male parent selection.
2. Plants of the new *Brachycome* are taller than plants of the male parent selection.
3. Plants of the new *Brachycome* have larger inflorescences than plants of the male parent selection.
4. Plants of the new *Brachycome* and the male parent selection differ in ray floret color as plants of the male parent selection have darker purple-colored ray florets.

Plants of the new *Brachycome* can also be compared to plants of the *Brachycome angustifolia* 'Billabong Mardi Gras', not patented. In side-by-side comparisons conducted in Cranbourne, Victoria, Australia, plants of the new *Brachycome* differed from plants of 'Billabong Mardi Gras' in the following characteristics:

1. Plants of the new *Brachycome* were taller and more mounding than plants of 'Billabong Mardi Gras'.

2. Plants of the new *Brachycome* were more vigorous than plants of 'Billabong Mardi Gras'.
3. Plants of the new *Brachycome* were more freely flowering than plants of 'Billabong Mardi Gras'.
4. Plants of the new *Brachycome* had larger and taller inflorescences than plants of 'Billabong Mardi Gras'.
5. Ray florets of plants of the new *Brachycome* were darker purple in color than ray florets of plants of 'Billabong Mardi Gras'.
6. Plants of the new *Brachycome* had longer peduncles than plants of 'Billabong Mardi Gras'.

BRIEF DESCRIPTION OF THE PHOTOGRAPHS

The accompanying colored photographs illustrate the overall appearance of the new *Brachycome* plant, showing the colors as true as it is reasonably possible to obtain in colored reproductions of this type. Colors in the photographs may differ slightly from the color values cited in the detailed botanical description which accurately describe the colors of the new *Brachycome* plant.

The photograph on the first sheet comprises a top perspective view of a typical flowering plant of 'Magenta Magic' grown in a container.

The photograph on the second sheet is a close-up view of typical inflorescences of 'Magenta Magic'.

DETAILED BOTANICAL DESCRIPTION

The aforementioned photographs and following observations, measurements and values describe plants grown during the spring and summer in 15-cm containers in a polyethylene-covered greenhouse in Cranbourne, Victoria, Australia and under commercial practice with day temperatures ranging from 12° C. to 40° C., night temperatures ranging from 6° C. to 28° C. and light levels ranging from 1,000 lux to 9,000 lux. Plants were pinched twice and were six months old when the photographs and description were taken. In the following description, color references are made to The Royal Horticultural Society Colour Chart, 1995 Edition, except where general terms of ordinary dictionary significance are used.

Botanical classification: *Brachycome angustifolia* 'Magenta Magic'.

Parentage:

*Female, or seed, parent.*—Proprietary selection of *Brachycome angustifolia* identified as code name OBAP176, not patented.

*Male, or pollen, parent.*—Proprietary selection of *Brachycome angustifolia* identified as code name OB04547, not patented.

Propagation:

*Type.*—By stem cuttings.

*Time to initiate roots, summer.*—About 12 to 25 days at temperatures of 22° C. to 30° C.

*Time to initiate roots, winter.*—About 18 to 35 days at temperatures of 15° C. to 22° C.

*Time to produce a rooted young plant, summer.*—About 20 to 30 days at temperatures of 16° C. to 39° C.

*Time to produce a rooted young plant, winter.*—About 25 to 45 days at temperatures of 10° C. to 20° C.

*Root description.*—Thin, fibrous; white in color.

*Rooting habit.*—Moderately freely branching; moderately dense.

Plant description:

*Plant form and growth habit.*—Compact, low spreading and mounded plant habit; moderately vigorous growth habit; freely branching habit with numerous lateral branches developing after pinching.

*Plant height.*—About 15 cm to 25 cm.

*Plant width (spread).*—About 25 cm to 60 cm.

*Lateral branches.*—Length: About 15 cm to 20 cm. Diameter: About 1.5 mm to 2 mm. Internode length: About 7 mm to 23 mm. Strength: Moderately strong; brittle when bent. Texture: Smooth, glabrous. Color: Close to 138A.

Foliage description:

*Arrangement.*—Alternate, simple; sessile.

*Length.*—About 1.8 cm to 6.5 cm.

*Width.*—About 5 mm to 25 mm.

*Shape.*—If lobe, narrowly cuneate; if entire, elliptic.

*Apex.*—Acute.

*Base.*—Attenuate.

*Margin.*—Entire to three to four-lobed; slightly undulate.

*Texture, upper and lower surfaces.*—Smooth, glabrous.

*Venation pattern.*—Pinnate.

*Color.*—Developing leaves, upper surface: Close to 137B. Developing leaves, lower surface: Close to 138A to 138B. Fully expanded leaves, upper surface: Close to 139A; venation, close to 139A. Fully expanded leaves, lower surface: Close to 137C; venation, close to 137C.

Inflorescence description:

*Appearance and habit.*—Single composite inflorescence form with ray and disc florets; inflorescences borne above the foliage; freely flowering habit with numerous inflorescences developing per plant during the flowering period.

*Fragrance.*—Not detected.

*Flowering season.*—Plants flower from spring through autumn in Australia; flowering continuous during this period; plants begin flowering about four to eight weeks after planting.

*Inflorescence longevity.*—Inflorescences last about two to four weeks on the plant; inflorescences not persistent.

*Inflorescence bud.*—Height: About 2 mm to 3 mm. Diameter: About 3 mm. Shape: Oblate. Color: Close to 71C and 148A.

*Inflorescence size.*—Height: About 7 mm to 8 mm. Diameter: About 2.8 cm to 3 cm. Diameter of disc: About 6 mm to 8 mm.

*Ray florets.*—Quantity/arrangement: About 15 to 22 in one to two whorls. Shape: Lanceolate to narrowly obovate. Apex: Bluntly acute. Base: Attenuate. Margin: Entire. Length: About 1.1 cm to 1.3 cm. Width: About 2 mm. Texture, upper and lower surfaces: Smooth, glabrous. Color: When opening, upper surface: Close to 63B. When opening, lower surface: Close to 63C. Fully opened, upper surface: Close to 78B. Fully opened, lower surface: Close to 78D.

*Disc florets.*—Arrangement: Massed at center of receptacle. Shape: Tubular, elongated. Apex: Five-pointed. Length: About 4 mm. Width: About 1 mm. Texture: Smooth, glabrous; satiny. Color, immature: Close to 144C. Color, mature: Close to 9A.

*Involucral bracts.*—Quantity/arrangement: About 16 to 20 arranged in a single whorl; bracts imbricate. Length: About 2 mm. Width: Less than 1 mm. Shape: Oblong; keeled and concave. Apex: Bluntly acute. Margin: Entire, fringed. Texture, upper surface:

Sparsely pubescent. Texture, lower surface: Smooth, glabrous. Color, upper surface: Between 139C and 137D. Color, lower surface: Close to 137D.

*Peduncles.*—Length: About 7.5 cm to 11 cm. Diameter: About 1 mm. Strength: Moderately strong. Texture: Smooth, glabrous. Color: Close to 137A.

*Reproductive organs.*—Present on disc florets only. Androecium: Filament length: About 2 mm. Filament color: Close to 155D. Anther length: Less than 1 mm. Anther shape: Oblong to lanceolate. Anther color: Close to 177A. Pollen amount: Scarce. Gynoecium: Stigma shape: Bi-lobed. Style length: About 2 mm. Style color: Close to 155D.

*Seeds.*—Seed set is nil to scarce on plants of the new *Brachycome*. Quantity per inflorescence: None to about three. Length: Less than 1 mm. Diameter: Less than 1 mm.

Disease/pest resistance: Plants of the new *Brachycome* have not been observed to be resistant to pathogens and pests common to *Brachycomes*.

Garden performance: Plants of the new *Brachycome* have been observed to have good garden performance and tolerate rain, wind and temperatures ranging from about −3° C. to about 45° C.

It is claimed:

1. A new and distinct *Brachycome* plant named 'Magenta Magic' as illustrated and described.

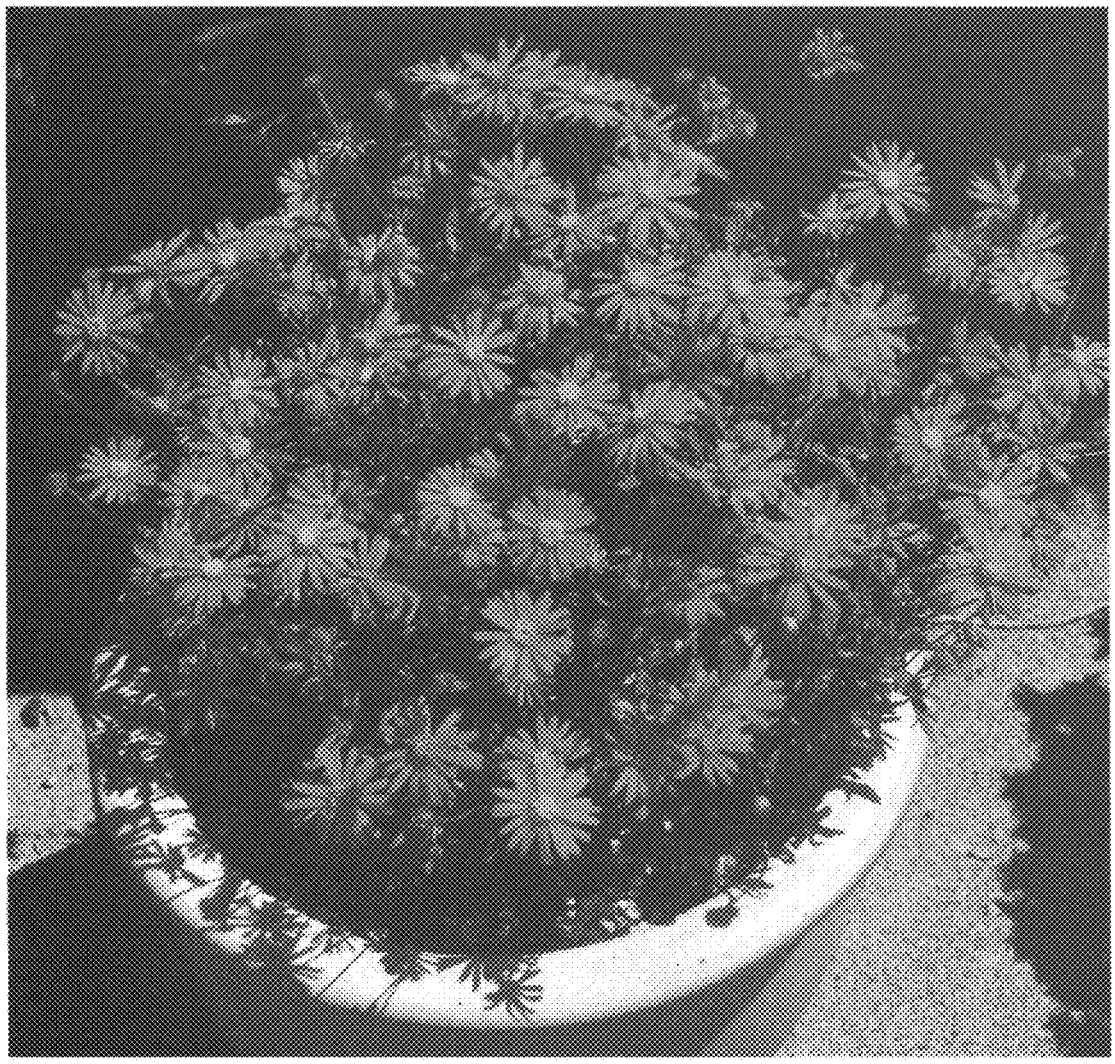

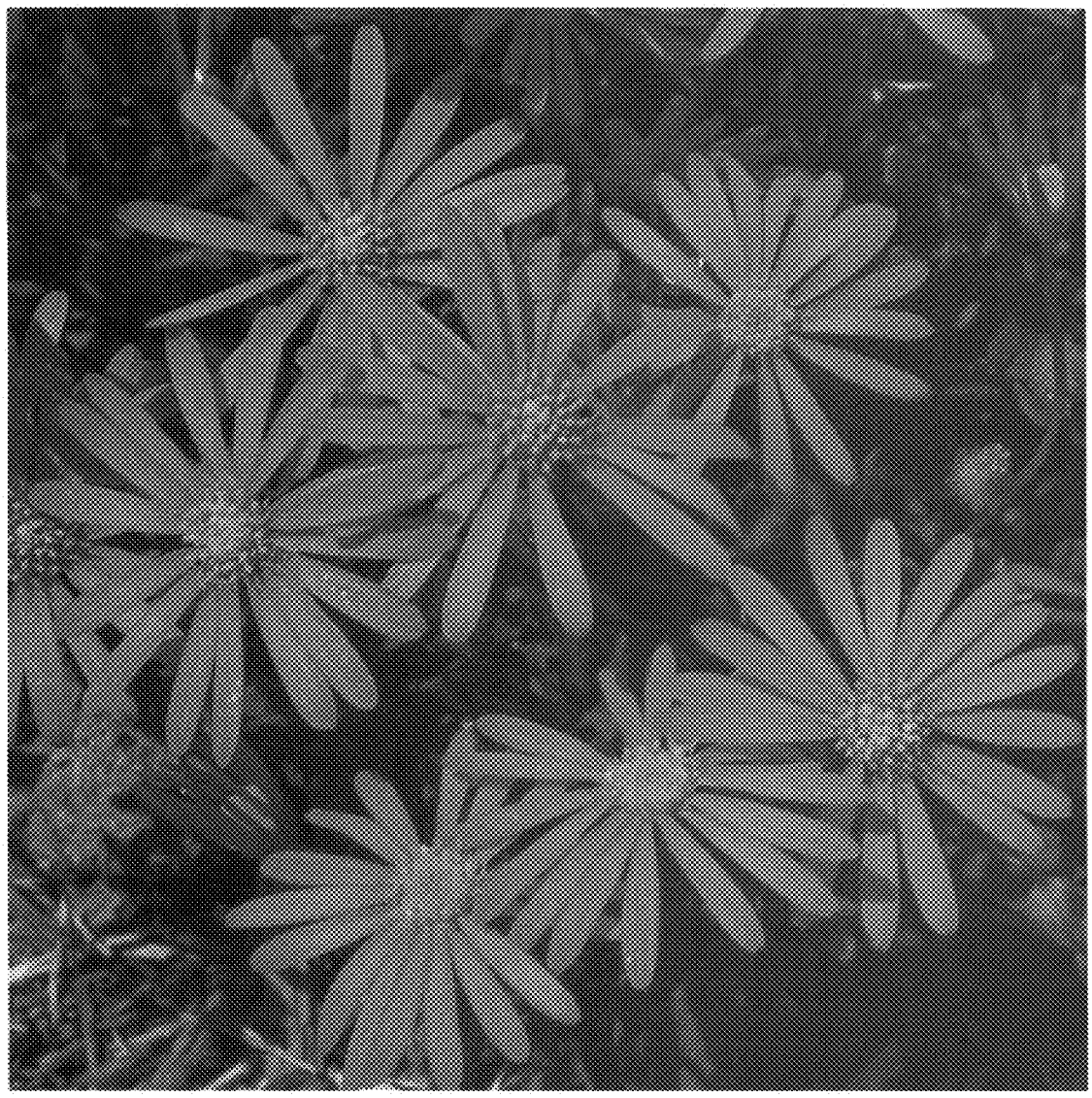

* * * * *